US012691291B2

(12) United States Patent
Doerr et al.

(10) Patent No.: US 12,691,291 B2
(45) Date of Patent: Jul. 28, 2026

(54) IMPLANTABLE MEDICAL DEVICE AND METHODS FOR MANUFACTURING AN IMPLANTABLE HOUSING

(71) Applicant: BIOTRONIK SE & Co. KG, Berlin (DE)

(72) Inventors: Thomas Doerr, Berlin (DE); Ingo Weiss, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 178 days.

(21) Appl. No.: 18/837,764

(22) PCT Filed: Feb. 14, 2023

(86) PCT No.: PCT/EP2023/053595
§ 371 (c)(1),
(2) Date: Aug. 12, 2024

(87) PCT Pub. No.: WO2023/161079
PCT Pub. Date: Aug. 31, 2023

(65) Prior Publication Data
US 2025/0161693 A1     May 22, 2025

(30) Foreign Application Priority Data
Feb. 24, 2022     (EP) .................................... 22158524

(51) Int. Cl.
*A61N 1/375*          (2006.01)
*A61N 1/05*           (2006.01)
*A61N 1/39*           (2006.01)
(52) U.S. Cl.
CPC ........... *A61N 1/375* (2013.01); *A61N 1/0504* (2013.01); *A61N 1/3956* (2013.01)

(58) Field of Classification Search
CPC ..... A61N 1/375; A61N 1/0504; A61N 1/3956
See application file for complete search history.

(56) References Cited

U.S. PATENT DOCUMENTS 6,370,427 B1 * 4/2002 Alt ....................... A61N 1/3962
607/121
2006/0217778 A1     9/2006 Strom et al.
(Continued)

FOREIGN PATENT DOCUMENTS

EP          0033242 A1     8/1981

OTHER PUBLICATIONS

Extended European Search Report mailed Aug. 17, 2022, by the European Patent Office for corresponding Application No. EP 22158524.3. (5 pages).
(Continued)

*Primary Examiner* — Rochelle D Turchen
(74) *Attorney, Agent, or Firm* — Buchanan Ingersoll & Rooney PC

(57)          ABSTRACT
An implantable medical device, in particular an extravascular cardioverter-defibrillator, comprises: an implantable housing for accommodating a control unit configured to generate and/or process electrical signals; wherein an outer surface of the housing comprises at least one electrode portion for receiving electrical signals to be processed by the control unit and/or for providing electrical signals generated by the control unit, the electrode portion being surrounded along its outer contour by an insulating portion which electrically insulates the electrode portion from a remainder of the housing; wherein both the electrode portion and the remainder of the housing are made of a biocompatible and electrically conductive first material; wherein the insulating portion is made of a biocompatible and electrically insulating second material comprising a titanium oxide compound.

15 Claims, 6 Drawing Sheets

(56)                    References Cited

U.S. PATENT DOCUMENTS

| | | |
|---|---|---|
| 2007/0106335 A1 | 5/2007 | Dal et al. |
| 2008/0183235 A1* | 7/2008 | Stancer .................. A61N 1/375 |
| | | 607/36 |
| 2012/0197366 A1 | 8/2012 | Zeijlemaker et al. |
| 2022/0021376 A1* | 1/2022 | Okamoto ........... H03K 3/02337 |

OTHER PUBLICATIONS

International Search Report (PCT/ISA/210) and Written Opinion (PCT/ISA/237) mailed May 11, 2023, by the European Patent Office as the International Searching Authority for International Application No. PCT/EP2023/053595. (8 pages).

* cited by examiner

IMPLANTABLE MEDICAL DEVICE AND METHODS FOR MANUFACTURING AN IMPLANTABLE HOUSING

CROSS-REFERENCE TO RELATED APPLICATIONS

This application is the United States National Phase under 35 U.S.C. § 371 of PCT International Patent Application No. PCT/EP2023/053595, filed on Feb. 14, 2023, which claims the benefit of European Patent Application No. 22158524.3, filed on Feb. 24, 2022, the disclosures of which are hereby incorporated by reference herein in their entireties.

TECHNICAL FIELD

The present invention relates to an implantable medical device, in particular an extravascular cardioverter-defibrillator. Furthermore, the present invention relates to methods for manufacturing an implantable housing for such a medical device.

BACKGROUND

A subcutaneous ICD system (ICD=implantable cardioverter-defibrillator) may include a subcutaneously implantable electrode lead having a shock coil for emitting electrical (shock) signals and a sensor electrode pole for sensing electrical signals in the body at each of the distal and proximal ends of the shock coil. A subcutaneously implantable (active) housing of the ICD system may function as an additional sensor electrode pole.

Due to afterpotentials occurring after a defibrillation shock, the housing usually needs to be excluded from signal acquisition for several seconds, so that only the two electrode poles on the electrode lead can temporarily be used after defibrillation. Thus, only one acquisition vector is available for this period of time. This problem can occur in stimulators whose housing is used for both delivery and sensing of electrical signals, as well as in unipolar stimulators in which electrical current flows between the housing and an electrode tip of the electrode lead.

For example, U.S. Publication No. 2007/0106335 A1 discloses an implantable housing for an implantable medical device configured to collect subcutaneous electrocardiogram (ECG) signals. The housing comprises on its outer surface one or more electrode portions for collecting those signals. Each electrode portion is formed by a stack of an electrically conductive top layer and an electrically insulating bottom layer. The bottom layer may be bonded to a planar surface of the housing, so that the top layer is electrically insulated by the bottom layer from the remainder of the housing. The top layer may be, for example, a platinum or platinum-iridium layer, whereas the remainder of the housing may be made of a different electrically conductive material such as titanium. Since the bottom layer and the housing are made of different materials, the bonding, especially by welding, may be difficult in some cases.

The present disclosure is directed toward overcoming one or more of the above-mentioned problems, though not necessarily limited to embodiments that do.

SUMMARY

It therefore may be seen as an objective of the present invention to provide an implantable medical device, in particular an extravascular cardioverter-defibrillator, with an improved implantable housing. Another objective of the present invention may be to provide improved methods for manufacturing an implantable housing for an implantable medical device, in particular an extravascular cardioverter-defibrillator.

At least these objectives may be achieved by the subject-matter of the independent claims. Advantageous embodiments are defined in the dependent claims as well as in the corresponding specification and figures.

A first aspect of the present invention relates to an implantable medical device, in particular an extravascular cardioverter-defibrillator, comprising: an implantable housing for accommodating a control unit configured to generate and/or process electrical signals; wherein an outer surface of the housing comprises at least one electrode portion for receiving electrical signals to be processed by the control unit and/or for providing electrical signals generated by the control unit, the electrode portion being surrounded along its outer contour by an insulating portion which electrically insulates the electrode portion from a remainder of the housing; wherein both the electrode portion and the remainder of the housing are made of a biocompatible and electrically conductive first material; wherein the insulating portion is made of a biocompatible and electrically insulating second material comprising a titanium oxide compound.

The implantable extravascular cardioverter-defibrillator may be a subcutaneously implantable device configured to perform, for example, cardioversion, defibrillation and/or pacing of the heart, impedance measurements or impedance communication. Unlike a transvenous ICD device, the electrode lead of the extravascular cardioverter-defibrillator is usually implanted under the skin above the breastbone, i.e., outside the heart and blood vessels, which are left untouched, whereas its housing is usually implanted on the left side of the chest next to the rib cage. Furthermore, the cardioverter-defibrillator may be suitable for magnetic resonance imaging (MRI).

Alternatively, the medical device may be, for example, a transvenous or intravenous ICD device or an implantable (extravascular) loop recorder.

The housing of the medical device may have one or more ports for connecting a distal end of the electrode lead. As mentioned above, the electrode lead may comprise a shock coil for providing electrical signals generated by the control unit and one or more electrode poles for sensing electrical signals to be processed by the control unit, e.g., for recording an electrocardiogram.

To increase the number of available sensing vectors, the housing may comprise, on its outer surface, one or more additional electrode poles for providing and/or sensing the electrical signals.

By electrically insulating the electrode pole(s) from the remainder of the housing, which is usually made of an electrically conductive (metal) material, the perceptual quality of the medical device can be significantly improved, especially immediately after shock delivery.

For example, the electrode portion(s) may be integrated into the outer surface of the housing in such a way that the outer surface has no significant elevations or depressions and the material thickness of the housing along the electrode portion(s) remains approximately the same as outside these electrode portion(s).

Optionally, the electrode portion(s) may be structured, e.g., by etching, laser treatment, mechanical roughening (such as sandblasting), and/or covered by one or more layers, e.g., comprising Pt—Ir, Ti or TiN, in order to increase its active surface, i.e., improve the lower frequency limit for electrical current flowing between the patient's body and the housing.

The insulating portion may be seen as a frame which may extend along the entire periphery of the electrode portion. Accordingly, the insulating portion may have an annular or ring-like shape. A width of the insulating portion, i.e., a dimension of the insulating portion in a direction transverse to the periphery of the electrode portion, may be sufficiently large such as to electrically isolate the electrode portion with respect to the remaining housing upon electric voltages typically applied by the ICD. For example, such width may be more than 0.1 mm, preferably more than 0.2 mm or more than 0.5 mm.

It may be that a respective thickness of the electrode portion(s) and/or of the insulating portion(s) corresponds to a thickness of the housing's (remaining) lateral wall. Particularly, a thickness of the insulating portion may be same or smaller than a thickness of a portion of the housing directly adjacent to the insulating portion.

A second aspect of the present invention relates to a method for manufacturing an implantable housing for the medical device as described above and below. The method comprises at least the following steps: providing the housing in a state to be oxidized, the housing being made of the first material; and generating the insulating portion made of the second material by locally oxidizing first material across a defined portion of an outer surface of the housing, thereby providing the electrode portion made of the first material. More specifically, the insulating portion may be generated in such a way that the outer surface of the housing comprises the electrode portion which is surrounded along its outer contour by the insulating portion which electrically insulates the electrode portion from the remainder of the housing.

This method may significantly simplify the provision of electrode portions on the surface of the housing. The method may also simplify the electrical contacting of components inside the housing.

A third aspect of the present invention relates to an alternative method for manufacturing an implantable housing for the medical device according to embodiments as described above and below. The method comprises at least the following steps: providing the body and the separate part in a state to be oxidized, both being made of the first material; generating the insulating portion made of the second material by locally oxidizing the first material across a defined portion of an outer surface of the separate part, thereby providing the electrode portion made of the first material; and bonding the oxidized separate part to the body to form the housing, so that the outer surface of the housing comprises the electrode portion. More specifically, the generating and bonding may be done in such a way that the outer surface of the housing comprises the electrode portion which is surrounded along its outer contour by the insulating portion which electrically insulates the electrode portion from the remainder of the housing.

This method may significantly simplify the provision of electrode portions on the surface of the housing. The method may also simplify the electrical contacting of components inside the housing.

Features of the medical device as described above and below may be considered to be features of these methods, and vice versa.

The oxidation may be seen as a controlled chemical process during which oxygen is introduced in a controlled manner locally into a substrate made of the first material, i.e., the housing or the separate part. The process may be such that the substrate is enriched with oxygen over part of its thickness or its entire thickness. If necessary, the thickness of the substrate may be reduced before and/or after oxidation, e.g., by removing material.

In a further step, the electrode portion(s) may be connected to one or more electrical contacts for electrically contacting the control unit. The contact(s) may be connected at one end to an exposed inner surface of the electrode portion(s). Electrical contacting of the electrode portion(s) on the inside of the housing may be achieved, for example, by bonding with conductive adhesive, soldering, welding or spring contacts.

Embodiments of the present invention may be considered, without limiting the present invention, as being based on the ideas and findings described below.

According to an embodiment, the first material may be titanium or titanium alloy. Titanium and titanium alloy are both known for their good biocompatibility and durability.

Additionally or alternatively, the titanium oxide compound may be titanium dioxide or barium titanate. Such titanium oxide compounds are relatively easy to provide, e.g., by oxidation of a substrate made of titanium or titanium alloy, and are known to have very good properties with respect to electrical insulation, biocompatibility and durability.

According to an embodiment, the electrode portion may have an exposed inner surface which is not covered by the insulating portion and faces an exposed outer surface of the electrode portion. A width of the exposed inner surface may differ from a width of the exposed outer surface by 50% or less, preferably by 25% or less, more preferably by 10% or less. The exposed surfaces may be, for example, planar surfaces parallel to each other. It is possible that at least one of the exposed surfaces is at least partially covered by at least one additional layer which is different from the insulating portion and/or from the first and/or second material. For example, the exposed inner surface may be at least partially covered by a reinforcing layer (see below). This embodiment may simplify electrical contacting of the electrode portion(s) via the exposed inner surface from the inside of the housing.

According to an embodiment, the housing may include a body and a separate part comprising the electrode portion and the insulating portion. The separate part may be bonded to the body. For example, the separate part may be used to cover and hermetically seal an opening in the body. Thus, the electrode portion(s) can be provided independently of the body of the housing. This may help to make manufacturing of the housing more efficient.

For example, the separate part may be a smaller area cut out of a larger piece of sheet metal (e.g., titanium) with a plurality of (prefabricated) electrode portions, each of which being surrounded along its outer contour by an insulating portion to form a plurality of electrically insulated islets. These islets may have the same shape and/or may be arranged in the same pattern and/or may have different shapes and/or may be arranged in different patterns. A desired area may then be cut out, as the separate part, of the sheet metal. This cutout may additionally be deformed in a controlled manner, e.g., by bending and/or deep drawing, before being bonded to the body, e.g., by welding and/or soldering.

According to an embodiment, the separate part may further comprise a connecting portion and be bonded to the body via the connecting portion. Both the body and the connecting portion may be made of the first material. The connecting portion may be a portion of the separate part outside the electrode portion and the insulating portion, e.g., surrounding the insulating portion along its outer contour. This may simplify the bonding process and improve the quality of the resulting connection, especially if the body and the separate part are to be welded together.

According to an embodiment, the separate part or specifically the connecting portion may be bonded to the body by welding and/or soldering. This may improve the durability of the bonding.

According to an embodiment, the insulating portion may have a planar surface which abuts at least one of a planar surface of the electrode portion or a planar surface of the remainder of the housing to form a continuous planar surface which is in contact with body tissue and/or body liquid when the housing is implanted. Particularly, an outer surface portion of the housing in an area formed by the insulating portion may preferably be flush with an outer surface portion of the housing in an area formed by the adjacent electrode portion and/or flush with an outer surface portion of the housing in an area formed by the adjacent remainder of the housing. This may further improve the perception qualities of the medical device. This also may allow for easier implantation of the housing into the patient's body.

According to an embodiment, the continuous planar surface may have a flatness defined by two parallel (imaginary) planes having a mutual distance of 0.1 mm or less, preferably 0.01 mm or less. Additionally, the mutual distance may be greater than 0.005 mm. The continuous planar surface may exclusively extend between those two planes. In other words, there may at most be an insignificant step at a transition between insulating portion and directly abutting adjacent portions of the housing.

According to an embodiment, the electrode portion may have a thickness of 0.4 mm or less, preferably 0.2 mm or less. Additionally or alternatively, the insulating portion may have a thickness of 0.4 mm or less, preferably 0.2 mm or less. This value ranges may correspond to the thickness of the housing's (remaining) lateral wall. In other words, at least one of the electrode portion(s) or the insulating portion(s) may have the same, or approximately the same, thickness as the housing's lateral wall.

According to an embodiment, the electrode portion may comprise a first stack of at least two layers made of the first material. Additionally or alternatively, the insulating portion may comprise a second stack of at least two layers made of the second material. This may simplify the manufacturing of the housing, especially any oxidation process used to provide the insulating portion(s) and, thus, the electrode portion(s). The layers of the first and/or second stack may, for example, be provided by additive manufacturing such as selective laser sintering (SLS) or electron-beam melting (EBM). It may be that each layer of the second stack is provided by oxidation of a defined portion of one of the layers of the first stack. Additionally, the second stack may comprise at least one layer made of a biocompatible and electrically insulating third material different from the second material, such as, for example, PEEK.

According to an embodiment, each layer of the first stack and/or of the second stack has a thickness of 0.2 mm or less, preferably 0.1 mm or less. If, as mentioned above, each layer of the second stack is provided by oxidation of a defined portion of one of the layers of the first stack, this embodiment may help to guarantee that each oxidized portion of the first layer is sufficiently enriched with oxygen over its entire thickness without having to remove excess material in an additional step.

According to an embodiment, at least one of the electrode portion or the insulating portion, on a side facing the inside of the housing, is at least partially covered by a reinforcing layer. The reinforcing layer may be made of an electrically insulating material. This may significantly improve the stability and durability of the housing without having to increase the thickness of the electrode portion(s) and/or of the insulating portion(s).

According to an embodiment, the electrode portion may comprise at least a first electrode portion and a second electrode portion as different portions of the outer surface of the housing. Accordingly, the insulating portion may comprise at least a first insulating portion surrounding the first electrode portion along its outer contour and a second insulating portion surrounding the second electrode portion along its outer contour. The different electrode portions may be viewed as islets electrically isolated from each other and from the remainder of the housing. To improve the sensing of electrical signals, it is advantageous if the electrode portions are as far away from each other as possible. For example, the electrode portions may be in diametrically opposite corner regions on the same side of the housing.

It has to be noted that possible features and advantages of embodiments of the present invention are described above and below partly with reference to an implantable medical device, partly with reference to corresponding manufacturing methods. A person skilled in the art will recognize that the features described for individual embodiments can be transferred, adapted and/or interchanged in an analogous and suitable manner to other embodiments in order to arrive at further embodiments of the present invention and possibly synergistic effects.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Advantageous embodiments of the present invention are further explained below with reference to the accompanying drawings. Neither the drawings nor the description are to be interpreted as limiting the present invention.

DETAILED DESCRIPTION

Figure 1:
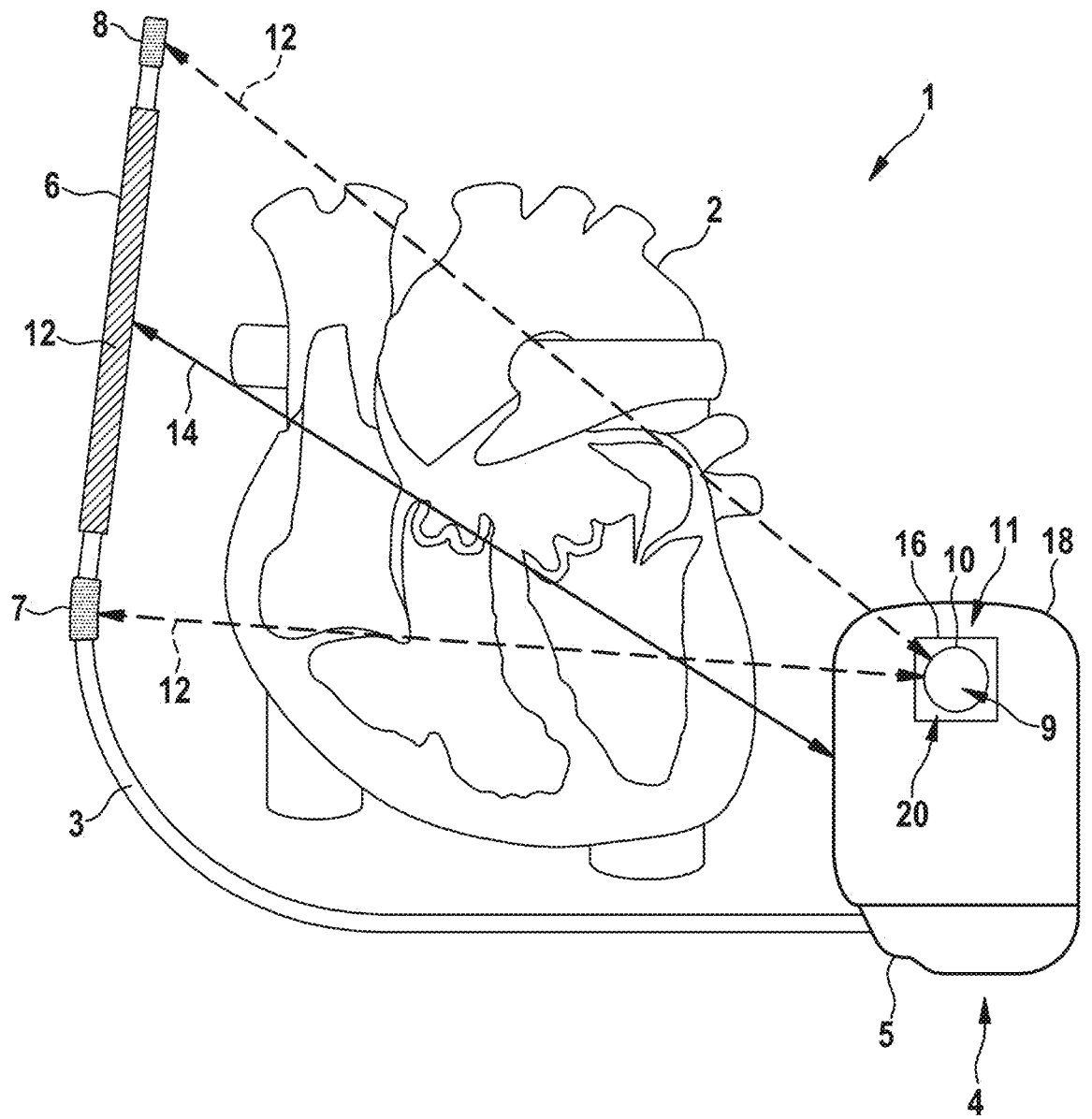
FIG. 1 shows a medical device according to an embodiment of the present invention.

FIG. 1 shows a medical device 1 in the form of an extravascular, i.e., non-transvenous cardioverter-defibrillator 1 implantable into a patient's body, e.g., for pacing of the patient's heart 2. The medical device 1 comprises an electrode lead 3 and an implantable housing 4 that accommodates a control unit (not shown), e.g., a pulse generator, configured to generate and process electrical signals.

The electrode lead 3, which is connected at its proximal end to a port 5 of the housing 4, has a shock coil 6 for providing electrical defibrillation shocks, a first sensing pole 7 at a proximal end of the shock coil 6 and a second sensing pole 8 at a distal end of the shock coil 6 for receiving electrical signals from the surrounding body tissue and/or body liquid.

The electrode lead 3 may be implanted left-parasternal or sternal, so that the shock coil 6 and the sensing poles 7, 8 are aligned on the sternum. In an area between the first sensing pole 7 and the port 5, the electrode lead 3 may be attached to the body tissue and lead at an angle to the left side of the thorax, where it is connected to the port 5.

The positions of the shock coil 6 and the housing 4 depend on the anatomical position of the heart 2 and should not be changed for effective defibrillation.

In addition to the sensing poles 7, 8, the housing 4 has an additional electrode pole in the form of an electrode portion 9, which is a portion of an outer surface of the housing 4.

The electrode portion 9 is surrounded along its outer contour by an insulating portion 10, here exemplary in the form of a closed ring, which electrically insulates the electrode portion 9 from a remainder 11 of the housing 4.

The electrode portion 9 and the remainder 11 of the housing 4 are made of the same biocompatible and electrically conductive material, which may be, for example, titanium or titanium alloy. The insulating portion 10, however, is made of a different biocompatible material having electrically insulating properties, such as, for example, titanium dioxide or barium titanate.

This has the effect that sensing vectors 12 between both sensing poles 7, 8 and between each of the sensing poles 7, 8 and the electrode portion 9 are not significantly affected by afterpotentials occurring after a shock delivery along a shocking vector 14 between the shock coil 6 and the housing 4. Thus, sensing functions are operable with respect to each of the three sensing vectors 12 without any restrictions immediately after shock delivery, i.e., without having to wait for the afterpotentials to decay. This may significantly improve the performance of the medical device 1.

Both the electrode portion 9 and the insulating portion 10 may be portions of a separate part 16 which may be bonded to a body 18, e.g., by laser welding, to form the hermetically sealed housing 4.

The separate part 16 may comprise a connecting portion 20 which may at least partially surround the insulating portion 10 along its outer contour. The separate part 16 may be bonded to the body 18 via the connecting portion 20. The connecting portion 20 and the body 18 (as well as the electrode portion 9) may be made of the same biocompatible and electrically conductive material, i.e., titanium or titanium alloy. This makes it easier to weld and/or solder both components together.

Figure 2:
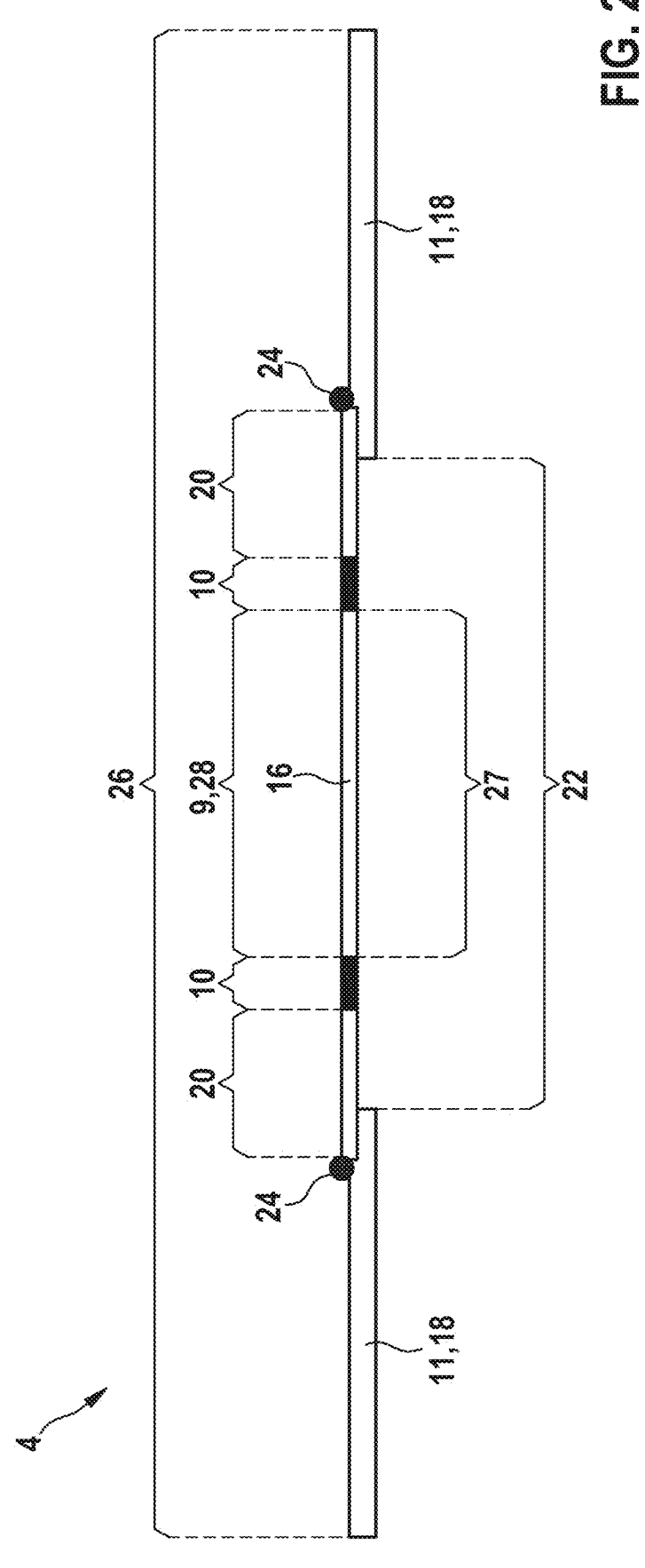
FIG. 2 shows a cross-sectional view of a portion of an implantable housing for a medical device according to an embodiment of the present invention.

As shown in FIG. 2, the separate part 16 may be placed over a relatively wide opening 22 in the body 18 and bonded to the body 18 via a circumferential laser welding seam 24 in such a way that the opening 22 is hermetically sealed.

The separate part 16, i.e., a combination of the electrode portion 9, the insulating portion 10 and the connecting portion 20, may have approximatively the same wall thickness as the body 18.

For example, as can be seen in FIG. 2, the electrode portion 9 may have a planar surface which abuts a planar surface of the insulating portion 10, the planar surface of the insulating portion 10 may abut a planar surface of the connecting portion 20, and the planar surface of the connecting portion 20 may abut a planar surface of the remainder 11 of the housing, i.e., of the body 18, so that a common planar surface 26 is formed, which is continuous, i.e., has no visible gaps or steps on its outside, and is part of the outer surface of the housing 4. Thus, the common planar surface 26 is in direct contact with body tissue and/or body liquid when the housing 4 is implanted.

The common planar surface 26, at least on its outside, may have a flatness defined by two parallel planes having a mutual distance of 0.1 mm or less, preferably 0.01 mm or less, more preferably 0.001 mm or less.

For example, the wall thickness of the housing 4, at least across the common planar surface 26, may be 0.4 mm or less, preferably 0.2 mm or less.

FIG. 2 further illustrates that the electrode portion 9, on its inner surface 27, may be exposed in so far as it is not covered by the insulating portion 10. Thus, the exposed inner surface 27 may approximately have the same width (in a direction transverse to its thickness) as an active outer surface 28 of the electrode portion 9. This makes it easier to electrically contact the electrode portion 9 from the inside of the housing 4. For example, the widths of the inner surface 27 and outer surface 28 may differ from each other by 50% or less, preferably by 25% or less, more preferably by 10% or less.

Figure 3:
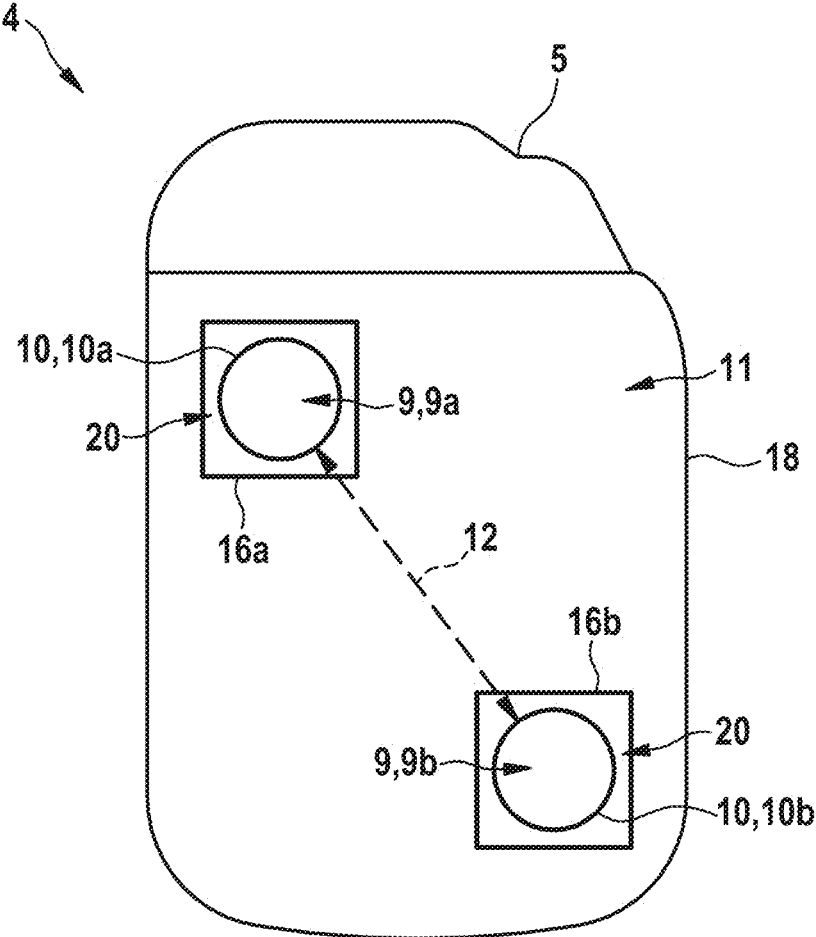
FIG. 3 shows an implantable housing for a medical device according to an embodiment of the present invention.

As shown in FIG. 3, it is possible that the electrode portion 9 comprises at least a first electrode portion 9a and a second electrode portion 9b as different portions of the outer surface of the housing 4. Accordingly, the insulating portion 10 may comprise at least a first insulating portion 10a surrounding the first electrode portion 9a along its outer edge and a second insulating portion 10b surrounding the second electrode portion 9b along its outer edge.

The first electrode portion 9a and the first insulating portion 10a may be portions of a first separate part 16a, whereas the second electrode portion 9b and the second insulating portion 10b may be portions of a second separate part 16b. Both separate parts 16a, 16b may be bonded to the body 18 in the same or a similar manner as described above referring to FIG. 1 and FIG. 2.

The electrode portions 9a, 9b may be placed at a maximum distance from each other on the outer surface of the housing 4. However, they should not protrude into a radius region of the housing 4. This maximizes a sensing vector 12 between the two electrode portions 9a, 9b. This also makes it possible to achieve a large vector difference when combining one of the two electrode portions 9a, 9b with one of the counter electrode poles 7, 8 of the electrode lead 3. Thus, a virtual repositioning of the housing 4 for sensing purposes can be achieved.

In this example, the electrode portions 9a, 9b are in diametrically opposite corner regions on the same side of the housing 4.

The housing 4 may additionally comprise one or more antennas for wireless data communication with external devices, e.g., for remotely transmitting the received and/or processed electrical signals.

Figure 4:
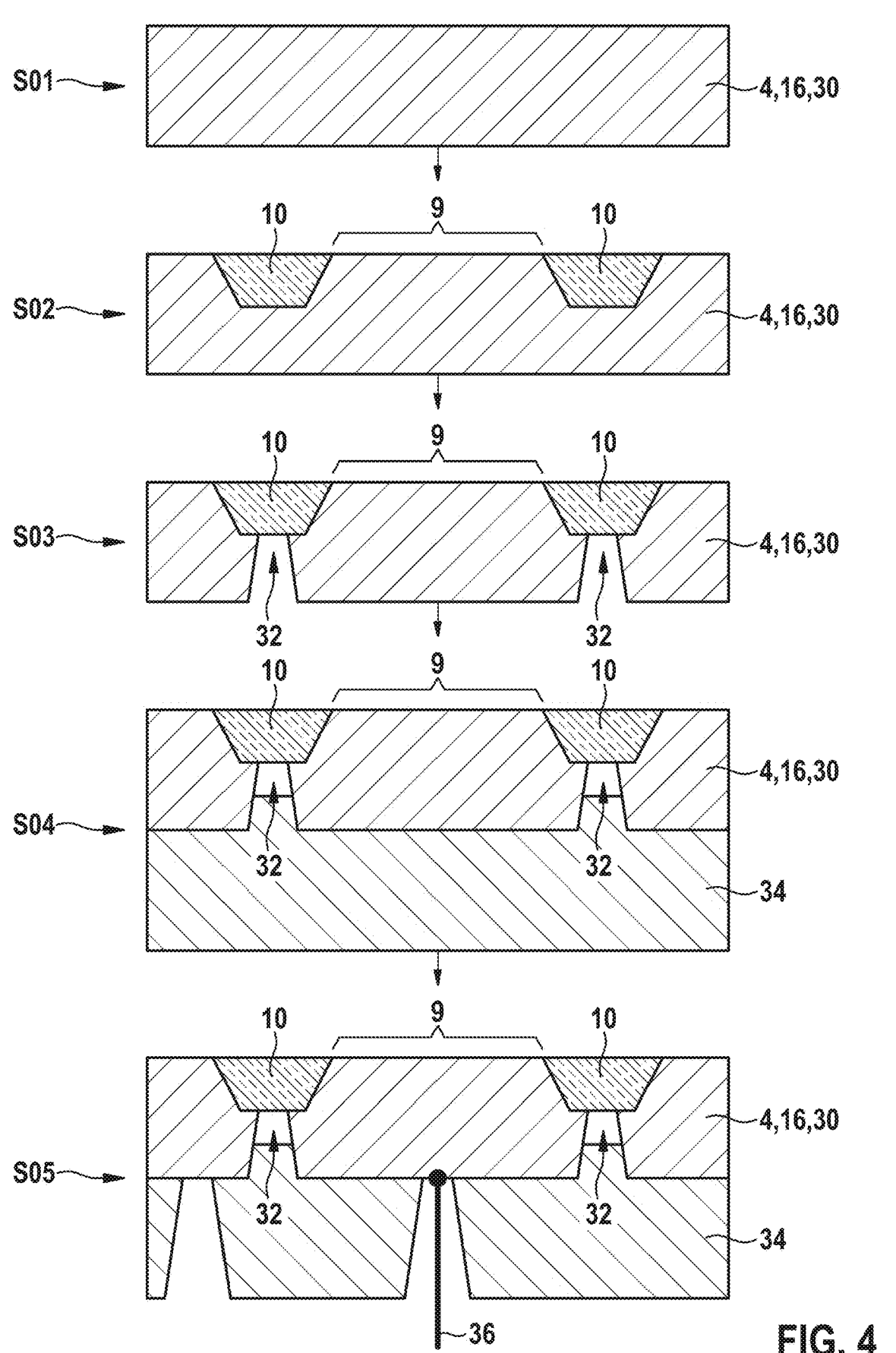
FIG. 4 illustrates steps of a method for manufacturing an implantable housing according to an embodiment of the present invention.

FIG. 4 illustrates steps of a method for manufacturing the housing 4.

In step S01, a substrate 30 made of titanium or titanium alloy is provided. The substrate 30 may be the (prefabricated) housing 4 or the separate part 16 in a state to be oxidized.

In step S02, the substrate 30 is oxidized across a defined portion of its outer surface to generate the insulating portion 10 (which corresponds to an oxidized portion of the substrate 30) and, thereby, the electrode portion 9. Accordingly, the insulating portion 10 may comprise a titanium oxide compound, for example, titanium dioxide or barium titanate.

The substrate 30 may be oxidized over part of its thickness, as shown here, or over its entire thickness (in this case, the substrate 30 should have an initial thickness of 0.2 mm or less, preferably 0.1 mm or less).

Optionally, in step S03, excess material, which has not been (sufficiently) enriched with oxygen in step S02, may be removed from the substrate 30, so that a recess 32 is formed on one side of the substrate 30 along the insulating portion 10. This may be done, for example, by etching, laser treatment or cutting with a waterjet.

For example, after step S03, the substrate 30 in the form of the oxidized separate part 16 may be bonded to the body 18 to form the housing 4. The body 18 may have been provided by bending and/or deep drawing a piece of the same material as the substrate 30 in its initial, i.e., non-oxidized state.

Additionally, in step S04, one or more reinforcing layers 34 may be applied at least partially on one side of the substrate 30, which corresponds to the inside of the housing 4, e.g., by lamination, vapor deposition or painting. The reinforcing layer(s) 34 may be electrically insulating and should be sufficiently rigid, at least in an area adjacent to the recess 32. For example, the recess 32 may be at least partially filled with the material of the reinforcing layer(s) 34. Optionally, the reinforcing layer(s) 34 may include reinforcing fibers.

Finally, in step S05, the electrode portion 9 may be electrically and mechanically connected to one or more contact elements 36 inside the housing 4. The contact element(s) 36 may at least partially run through the reinforcing layer(s) 34.

Figure 5:
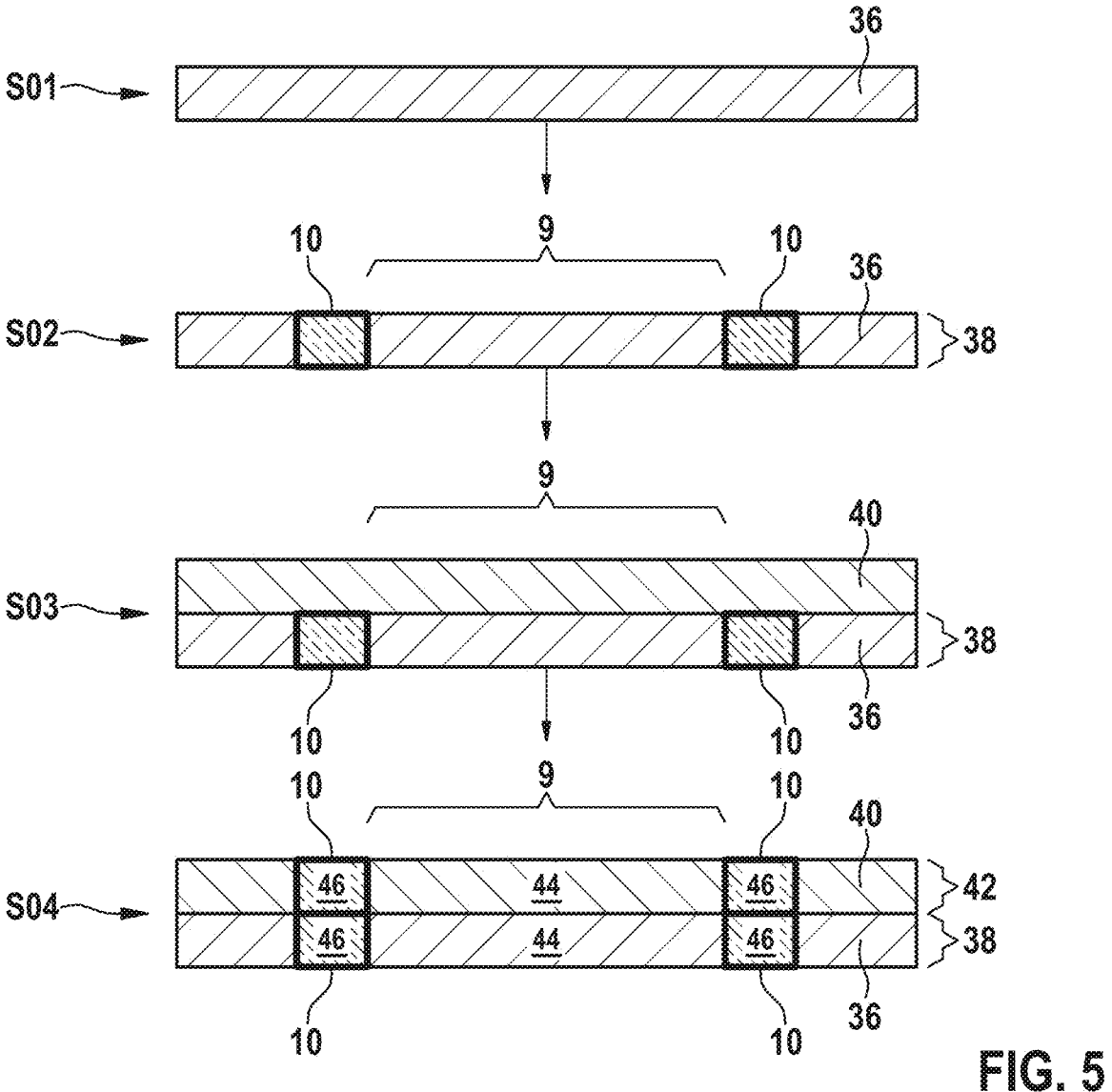
FIG. 5 illustrates steps of a method for manufacturing an implantable housing according to an alternative embodiment of the present invention.

An alternative method is shown in FIG. 5. The foils and/or layers as described in the following may be foils and/or layers of a lateral wall of the housing 4 and/or of the separate part 16.

In step S01, a first titanium foil 36 with a thickness of 0.1 mm or less may be provided.

In step S02, the first titanium foil 36 may be oxidized over its entire thickness across a defined portion of its surface to generate the insulating portion 10 and the electrode portion 9 as different portions of a first (partly) oxidized layer 38.

In step S03, a second titanium foil 40, which may have the same thickness as the first titanium foil 36, may be applied onto the first oxidized layer 38.

The titanium foils 38, 40 may be layered on top of each other in such a way that they are electrically and mechanically well connected to each another, for example, by rolling, (resistance) welding, electrically conductive bonding, vapor deposition, laser sintering, electron beam sintering or in another suitable additive manufacturing process.

In step S04, the second titanium foil 40 may be oxidized over its entire thickness across a defined portion of its surface to generate the insulating portion 10 and the electrode portion 9 as different portions of a second (partly) oxidized layer 42. The second titanium foil 40 may be oxidized in such a way that the electrode portion 10 of the first oxidized layer 38 overlaps with the electrode portion 9 of the second oxidized layer 42 and the insulating portion 10 of the first oxidized layer 38 overlaps with the insulating portion 10 of the second oxidized layer 42.

As a result, the electrode portion 9 may comprise a stack of at least two layers 44 made of the same titanium or titanium alloy material, and the insulating port 10 may comprise a stack of at least two layers 46 made of the same titanium oxide material.

Step S03 and step S04 may be repeated at least one more time to obtain a stack of at least three (partly) oxidized layers, which has the desired overall thickness.

Additionally, one or more reinforcing layers 34 may be applied on one side of the stack in the same or a similar manner as described above referring to FIG. 4.

Figure 6:
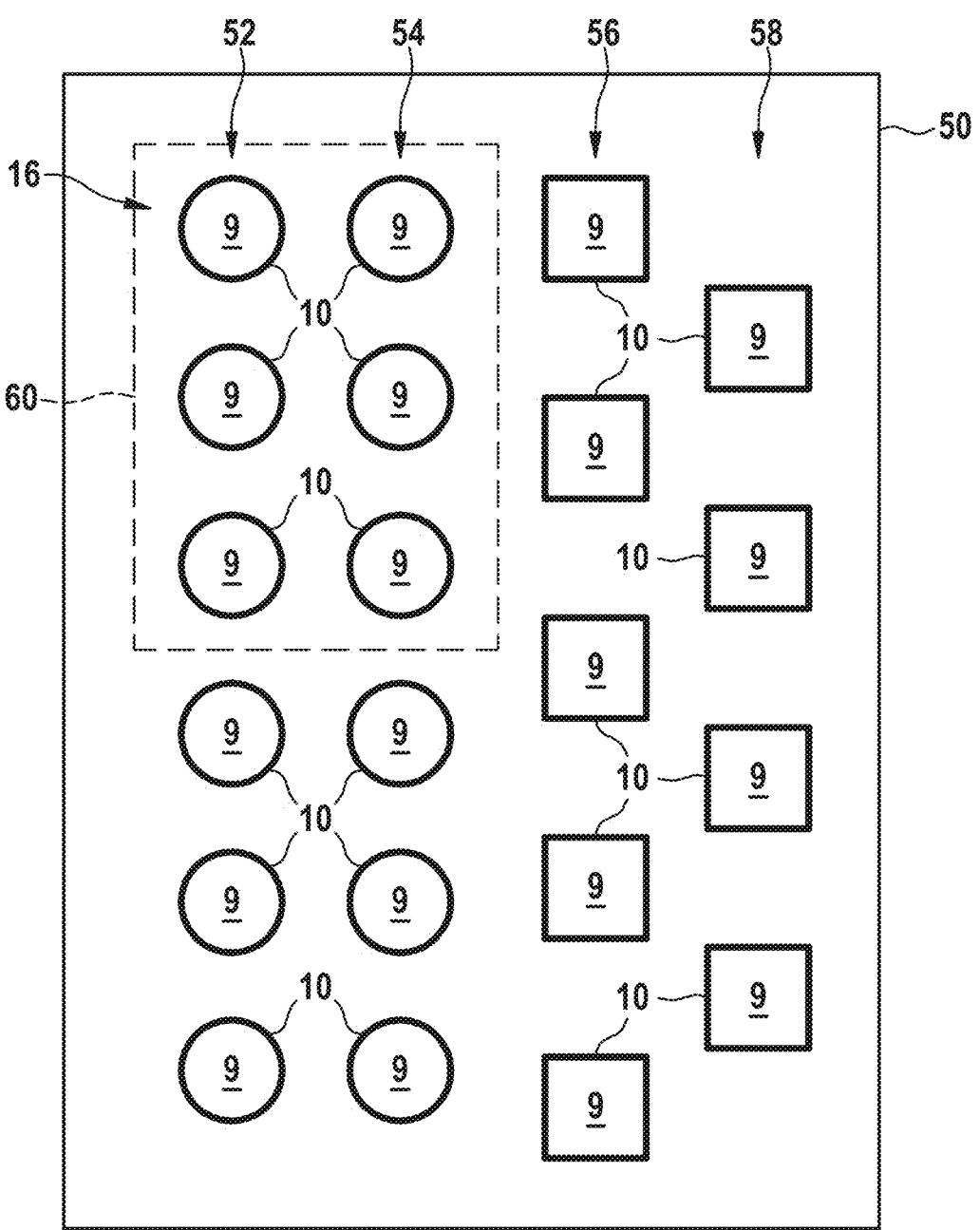
FIG. 6 shows a piece of sheet metal comprising a plurality of electrode portions prefabricated with a method according to an embodiment of the present invention.

As shown in FIG. 6, the separate part 16 may have been cut out of a larger piece of sheet metal 50, here a rectangular piece made of titanium, comprising a plurality of prefabricated electrode portions 9, each of which being surrounded along its outer contour by an insulating portion 10, which may be made of titanium dioxide, and, thus, forming an islet electrically insulated from the other electrode portions 9.

For example, the piece of sheet metal 50 may have a length of several meters.

The electrode portions 9 may have different outer contours such as, for example, circular, ellipsoidal, square or rectangular outer contours.

Furthermore, the electrode portions 9 may be arranged in one or more specific patters on the piece of sheet metal 50. For example, the electrode portions 9 may be arranged in two or more rows and/or in two or more columns on the piece of sheet metal 50.

In this example, the electrode portions 9 are arranged in a first column 52, a second column 54, a third column 56 and a fourth column 58. The first column 52 and the second column 54 each comprise a plurality of circular electrode portions 9. The third column 56 and the fourth column 58 each comprise a plurality of square electrode portions 9. Furthermore, the electrode portions 9 of the third column 56 are vertically offset with respect to the electrode portions 9 of the fourth column 58. The separate part 16 is cut out along a rectangular cutting line 60 and comprises six electrode portions 6, i.e., three from each of the first column 52 and the second column 54.

The cut out separate part 16 may additionally be deformed in a controlled manner, e.g., by bending and/or deep drawing, before being bonded to the body 18, e.g., by welding.

It has to be noted that, in the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope of the claims.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. An implantable medical device, in particular an extravascular cardioverter-defibrillator, comprising:
   an implantable housing for accommodating a control unit configured to generate and/or process electrical signals;
   wherein an outer surface of the housing-comprises at least one electrode portion for receiving electrical signals to be processed by the control unit and/or for providing electrical signals generated by the control unit, the electrode portion being surrounded along its outer contour by an insulating portion which electrically insulates the electrode portion from a remainder of the housing;
   wherein both the electrode portion and the remainder of the housing are made of a biocompatible and electrically conductive first material;
   wherein the insulating portion is made of a biocompatible and electrically insulating second material comprising a titanium oxide compound.

2. The medical device of claim 1,
   wherein the first material is titanium or titanium alloy; and/or
   wherein the titanium oxide compound is titanium dioxide or barium titanate.

3. The medical device of claim 1, wherein the electrode portion has an exposed inner surface which is not covered by the insulating portion and faces an exposed outer surface which is not of the electrode portion, a width of the exposed inner surface differing from a width of the exposed outer surface by 50% or less, preferably by 25% or less, more preferably by 10% or less.

4. The medical device of claim 1, wherein the housing includes a body and a separate part comprising the electrode portion and the insulating portion; wherein the separate part is bonded to the body.

5. The medical device of claim 4,
   wherein the separate part further comprises a connecting portion and is bonded to the body via the connecting portion;
   wherein both the body and the connecting portion are made of the first material.

6. The medical device of claim 4,
   wherein the separate part is bonded to the body by welding and/or soldering.

7. The medical device of claim 1, wherein the insulating portion has a planar surface which abuts a planar surface of the electrode portion and/or a planar surface of the remainder of the housing to form a continuous planar surface which is in contact with body tissue and/or body liquid when the housing is implanted.

8. The medical device of claim 7,
   wherein the continuous planar surface has a flatness defined by two parallel planes having a mutual distance of 0.1 mm or less, preferably 0.01 mm or less.

9. The medical device of claim 1,
   wherein the electrode portion has a thickness of 0.4 mm or less, preferably 0.2 mm or less; and/or
   wherein the insulating portion has a thickness of 0.4 mm or less, preferably 0.2 mm or less.

10. The medical device of claim 1,
    wherein the electrode portion comprises a first stack of at least two layers made of the first material; and/or
    wherein the insulating portion comprises a second stack of at least two layers made of the second material.

11. The medical device of claim 10,
    wherein each layer of the first stack and/or of the second stack has a thickness of 0.2 mm or less, preferably 0.1 mm or less.

12. The medical device of claim 1,
    wherein at least one of the electrode portion and the insulating portion, on a side facing the inside of the housing, is at least partially covered by a reinforcing layer.

13. The medical device of claim 1,
    wherein the electrode portion comprises at least a first electrode portion and a second electrode portion as different portions of the outer surface of the housing;
    wherein the insulating portion comprises at least a first insulating portion surrounding the first electrode portion along its outer contour and a second insulating portion surrounding the second electrode portion along its outer contour.

14. A method for manufacturing an implantable housing for the medical device of claim 1, the method comprising:
    providing the housing in a state to be oxidized, the housing being made of the first material; and
    generating the insulating portion made of the second material by locally oxidizing the first material across a defined portion of an outer surface of the housing thereby providing the electrode portion made of the first material.

15. A method for manufacturing an implantable housing for the medical device of claim 4, the method comprising:
    providing the body and the separate part in a state to be oxidized, both being made of the first material;
    generating the insulating portion made of the second material by locally oxidizing the first material across a defined portion of an outer surface of the separate part, thereby providing the electrode portion made of the first material; and
    bonding the locally oxidized separate part to the body to form the housing.

* * * * *